United States Patent [19]

Giersch et al.

[11] 4,255,292
[45] Mar. 10, 1981

[54] PERFUMING COMPOSITION CONTAINING 3-PHENYL-CYCLOHEX-2-EN-1-ONE

[75] Inventors: Wolfgang Giersch; Günther Ohloff, both of Bernex, Switzerland

[73] Assignee: Firmenich SA, Geneva, Switzerland

[21] Appl. No.: 75,418

[22] Filed: Sep. 14, 1979

[30] Foreign Application Priority Data

Sep. 27, 1978 [CH] Switzerland ............... 10058/78

[51] Int. Cl.$^3$ ............................................... C11C 9/00
[52] U.S. Cl. ............................................... 252/522 R
[58] Field of Search ................................. 252/522 R

[56] References Cited
U.S. PATENT DOCUMENTS 4,144,200  3/1979  Sundt et al. ............... 252/522 R

FOREIGN PATENT DOCUMENTS 7021701  7/1978  Japan.

OTHER PUBLICATIONS

Steffen Arctauder, Perfume and Flavor Chemicals, published by author, Montclair, N. J., Monographs 789 and 790, 1969.
Norman C. Ross et al., J. Org. Chem., 29, 2341–2346, 1964.

Primary Examiner—Veronica O'Keefe
Attorney, Agent, or Firm—Pennie & Edmonds

[57] ABSTRACT

Perfuming composition containing 3-phenyl-cyclohex-2-en-1-one as active ingredient. Process for the perfuming of cosmetic articles, soaps and detergents by making use of the said ketone compound.

1 Claim, No Drawings

PERFUMING COMPOSITION CONTAINING 3-PHENYL-CYCLOHEX-2-EN-1-ONE

THE INVENTION

The present invention relates to perfumery, more particularly it relates to the use of a ketone derivative, 3-phenyl-cyclohex-2-en-1-one, as active ingredient in the process for the perfuming of cosmetic articles, soaps and detergents.

The invention provides also a perfuming composition containing 3-phenyl-cyclohex-2-en-1-one as active ingredient.

The cited phenyl-cyclohexenone is a known chemical entity, it has been namely described in Japanese Pat. No. 70 21, 701 wherein its use as intermediate for the preparation of a pharmaceutical compound has been disclosed.

Other literature sources disclose the preparation of the said phenyl-cyclohexenone starting from 1,5-diketones, viz. 1-phenyl-hexane-1,5-dione, this latter derivative being synthetized by condensing acetophenone with methyl vinyl ketone [J. Org. Chem. 29, 2341 (1964)]. Sofar however no suggestion has been formulated concerning the possible use of its as perfumant.

We have now surprisingly discovered that 3-phenyl-cyclohex-2-en-1-one possesses a powerful warm and spicy scent, whose character is reminiscent of the spicy one of coumarin without however possessing its typical hay-wood-ruff note.

Among the variety of compounds presenting a certain structural analogy with the cited phenyl-cyclohexenone, one may cite 2- and 4-cyclohexyl-cyclohexanone. These two compounds possess a herbaceous, minty, woody note; however they have found little utility in perfumery [see S. Arctander, Perfume and Flavor Chemicals, Secs. 789 and 790, Montclair, USA (1969)].

Owing to its particular odorous properties, 3-phenyl-cyclohex-2-en-1-one finds a very broad spectrum of applications, particularly in compositions of chypre, fougere and lavender type, or generally in compositions destined to the manufacture of perfuming articles of masculine type. It can also be conveniently used to perfume technical or cosmetic materials, e.g. detergents, soaps or house-hold materials. Depending on the nature of the perfumed materials or on the effect desired, the proportions used may vary within a wide range and may be, for example, of the order of about 1 to 10% by weight, based on the total weight of said perfumed materials. It has to be understood however that said concentrations are not deemed to represent absolute values and proportions higher or lower than those given above may also be used. Lower concentrations may namely be utilized in the manufacture of perfumed products such as soaps, cosmetics, detergents and house-hold materials in general.

3-Phenyl-cyclohex-2-en-1-one can be prepared in accordance with known methods, for instance according to the method described in J. Indian Chem. Soc., 12 62 (1935), or, alternatively, starting from cyclohexane-1,3-dione as shown by the following reaction parthway [see also: J. Am. Chem. Soc., 70, 2174 (1948)].

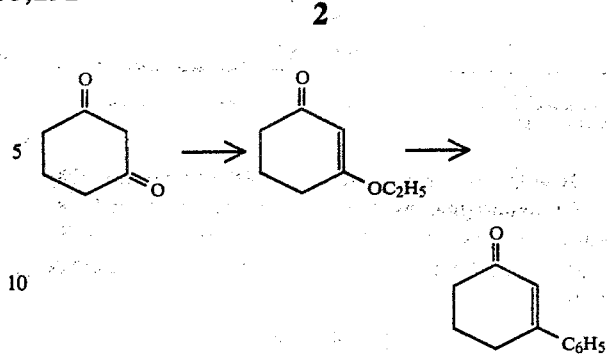

The method followed is indicated in details hereinbelow.

a. A mixture of 179 g of cyclohexane-1,3-dione, 4 g of p-toluenesulfonic acid, 850 ml of anhydrous ethanol and 41 ml of toluene was refluxed in a reactor equipped with a Vigreux distillation column. The volatile fraction (bp 74°–100°/730 Torr) was collected during 11 hours, then the mixture was cooled, washed with a diluted aqueous NaOH solution, concentrated and distilled to give 194 g (yield 87%) of a fraction having b.p. 115°/9 Torr;

IR: 1635 $cm^{-3}$

NMR: 1.36 (3H, t, J=7 Hz); 3.91 (2H, q, J=7 Hz); 5.33 (1H, s) δ ppm.

b. A solution of 15.7 g of bromobenzene in 100 ml of ether was added dropwise to a well stirred suspension of magnesium turnings in diethylether. Once upon termination of the addition, the reaction mixture was refluxed for 15 minutes, then, after cooling, there was slowly added a solution of 10 g of the enol-ether obtained sub letter a. above in 100 ml of diethyl ether. The reaction was exothermic.

The mixture was then refluxed for 15 supplementary minutes, whereupon it was cooled and poured onto a mixture of HCl and ice and the ethereal layer was separated and washed with water until neutrality. Evaporation of the organic phase followed by bulb distillation yielded 10.5 g (yield 86%) of the desired product: b.p. 150° (bath temperature)/0.01 Torr. The product was purified by crystallization in diethyl ether. M.p. 65°–6°

IR (neat): 1640 $cm^{-1}$

NMR: 1.9—2.9 (6H, m); 6.4 (1H, t, J=1 Hz); 7.3 (5H, m) δ ppm;

MS: M+ =172 (73); m/e: 154 (12), 144 (100), 166 (58), 115 (62), 102 (7), 89 (5), 77 (7), 71 (5), 63 (6), 51 (9), 39 (9).

The temperatures given above are indicated in degrees centigrade.

The invention is better illustrated by the following examples.

EXAMPLE 1

Perfuming composition

A base perfuming composition of lavender type was prepared by mixing together the following ingredients (parts by weight):

| | |
|---|---|
| Lavandin oil | 450 |
| Lavender oil | 200 |
| Cyclopentadecanolide 10%* | 100 |
| Synthetic grey amber, infusion 3%* | 100 |
| Bergamot oil | 50 |
| Lavender absolute | 50 |
| Clary-sage oil | 50 |

| -continued | |
|---|---|
| Total | 1000 |

*in diethyl phthalate

By adding to 98 g of the above base composition, 2 g of 3-phenyl-cyclohex-2-en-1-one, there was obtained a novel composition possessing, by comparison with the base composition, a more spicy and tenacious odorous note.

EXAMPLE 2

Perfumed soap

A commercial soap paste was perfumed by adding to it 0.1 to 0.2% by weight of 3-phenyl-cyclohex-2-en-1-one. The product thus obtained possessed an agreable spicy note, which note masked well the fatty ordour of the soap paste.

EXAMPLE 3

Perfuming composition

A base perfuming composition of fourgère type was prepared by mixing the following ingredients (parts by weight):

| | |
|---|---|
| Lavandin oil | 200 |
| Synth.geranium oil | 100 |
| Cedar wood oil of Texas | 80 |
| -continued | |
|---|---|
| Concrete oak-moss 50%* | 80 |
| Benzyl salicylate | 60 |
| Terpenyl acetate | 60 |
| Linalol | 50 |
| Amyl salicylate | 40 |
| Linalyl acetate | 40 |
| Patchouli oil | 40 |
| Isobutyl benzoate | 30 |
| Terpineol | 20 |
| Aspic oil | 20 |
| Clove oil | 20 |
| Musk ambrette | 20 |
| Musk xylene | 20 |
| Geraniol | 20 |
| Galbanum resin | 10 |
| Phenylacetaldehyde-dimethylacetal | 10 |
| Total | 920 |

*in diethyl phthalate

By adding to 92 g of the said composition 8 g of coumarin, there was obtained a novel composition of classical fougere type. By adding to 92 g of the base composition, 8 g of 3-phenyl-cyclohex-2-en-1-one, there was obtained a composition which, by comparison with that containing coumarin, possessed a less spicy character and a marked "hay-silo" note.

What we claim is:

1. A process for improving, enhancing, or modifying the odorous properties of a perfume, or a perfume base which comprises adding thereto a perfuming effective amount of 3-phenyl-cyclohex-2-en-1-one to impart a warm and spicy scent reminiscent of courmarin thereto.

* * * * *